US00PP24355P2

(12) United States Plant Patent
Korlipara

(10) Patent No.: US PP24,355 P2
(45) Date of Patent: Mar. 25, 2014

(54) ***ECHINACEA* PLANT NAMED 'CINNAMON CUPCAKE'**

(50) Latin Name: ***Echinacea* spp.**
Varietal Denomination: Cinnamon Cupcake

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 59 days.

(21) Appl. No.: 13/573,341

(22) Filed: Sep. 11, 2012

(51) Int. Cl.
*A01H 5/00* (2006.01)

(52) U.S. Cl.
CPC ..... *A01H 5/00* (2013.01)
USPC ..... Plt./428

(58) Field of Classification Search
CPC ..... A01H 4/00; A01H 5/00; A01H 1/00; A01H 1/04; A01H 1/06
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Cinnamon Cupcake' characterized by red to red orange ray florets, enlarged red disc florets forming an anemone-type inflorescence, contrasting dark stems, a multicrown, dwarf habit with strong upright stems, and excellent vigor.

1 Drawing Sheet

Botanical denomination: *Echinacea* spp.
Variety designation: 'Cinnamon Cupcake'.

BACKGROUND OF THE INVENTION

The present invention relates to a new and distinct cultivar of *Echinacea* and given the cultivar name 'Cinnamon Cupcake'. *Echinacea* is in the family Asteraceae. This new cultivar is a fourth generation seeding from a planned breeding program for double anemone flowered dwarf *Echinacea*. The exact parents of this selection are unknown, unnamed, proprietary plants.

Compared to *Echinacea purpurea* 'Cranberry Cupcake', U.S. Plant Pat. No. 23,020, the new cultivar has cinnamon red flowers rather than cranberry pink.

Compared to *Echinacea* 'Secret Love' U.S. Plant patent application Ser. No. 13/573,349, the new cultivar is shorter.

Compared to *Echinacea* 'Hot Papaya' (U.S. Plant Pat. No. 21,022), the new cultivar is shorter and more compact, has more crowns, more inflorescences per stem, and an inflorescence that is more red in color.

This new *Echinacea* cultivar is distinguished by:

1. red to red orange ray florets,
2. enlarged red disc florets forming an anemone-type inflorescence,
3. contrasting dark stems,
4. a multicrown, dwarf habit with strong upright stems, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the inflorescences and habit of a two-year-old *Echinacea* 'Cinnamon Cupcake' in the trial field in full sun in mid-July in Canby, Oreg. A black background was dropped behind the plant to show the habit.

FIG. 2 shows a close up of the flowers.

DETAILED PLANT DESCRIPTION

The following is a detailed description of the new *Echinacea* cultivar based on observations of a three-year-old specimen growing in the ground in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type*.—Herbaceous perennial.

*Hardiness*.—USDA Zones 4 to 9.

*Size*.—Grows to about 40 cm wide and 41 cm tall to top of inflorescences.

*Form*.—Basal clump, with about 35 stems from the base.

*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 0 to 2 flowering branches off the main flowering stems.

*Size*.—To 39 cm tall to a terminal inflorescence and 4 mm wide at base.

*Internode length.*—2.5 cm to 3.5 cm.
*Surface texture.*—Strigose.
*Color.*—Greyed Purple 187A.

Leaf (basal):
*Type.*—Simple.
*Shape.*—Lanceolate.
*Arrangement.*—Basal.
*Blade size.*—Grows to 7 cm long and 2.5 cm wide.
*Margins.*—Serrate, slightly undulate.
*Apex.*—Acute.
*Base.*—Attenuate.
*Surface texture.*—Strigose on both sides.
*Venation.*—Pinnate with three main veins from near the base, Yellow Green 147C on top and 146C on bottom.
*Color.*—Closest to: topside, Yellow Green 147A, bottom side Yellow Green 147B.
*Petiole description.*—Grows to 10 cm long and 2 mm wide, strigose, Yellow Green 147C tinted Greyed Purple 187A.

Leaf (stem):
*Type.*—Simple.
*Shape.*—Lanceolate.
*Arrangement.*—Alternate.
*Blade size.*—Grows to 8 cm long and 2.8 cm wide.
*Margins.*—Entire, slightly undulate.
*Apex.*—Acuminate.
*Base.*—Attenuate.
*Surface texture.*—Strigose on both sides.
*Venation.*—Pinnate with three main veins from near the base, Yellow Green 147C on top and 146C on bottom.
*Color.*—Closest to: topside, Yellow Green 147A, bottom side Yellow Green 147B.
*Petiole description.*—Grows to 5 cm long and 2 mm wide, strigose, Yellow Green 147C tinted Greyed Purple 187A near the base.

Inflorescence:
*Type.*—Composite on terminal stalked heads.
*Number of flowering stems from the ground.*—About 35.
*Flowering stem.*—Grows to 39 cm tall from the base of the plant to the terminal inflorescence and can grow to 9 cm long from the top stem leaf to the base of an inflorescence; sometimes branched, with 1 to 2 inflorescences per stem; diameter growing to 6 mm wide near the inflorescence; strigose; Greyed Purple 187A.
*Size.*—Grows to 4.5 cm wide and 5 cm deep as disc enlarges.
*Form.*—Ray florets held reflexed, mature disc is conic.
*Immature inflorescence.*—Grows to 4 cm wide and 1.5 cm deep, ray florets held slightly upright and rolled up so only the back color shows, Greyed Red 178B, disc color two toned Greyed Red 181 A where florets opening and Greyed Purple 187A where florets closed.
*Ray florets.*—Without pistil or stamen, about 16 full size, grow to 35 mm long and 6 mm wide, oblanceolate with the tip two toothed (each acute), entire margins, base attenuate, glabrous on both sides; topside color Orange Red N34 on bottom half lightening to 34C near apex, bottom side Greyed Red 178B.
*Disc.*—Flat becoming conic, becoming 27 mm deep and 50 mm wide with maturity, overall color is Red 46A.
*Disc florets.*—About 350 in number, each with 1 pistil and 4 stamen, grow to 17 mm long and 4 mm wide, each with one persistent bract (10 mm long with the top 2 mm colored Greyed Purple 187A on tip then 1 mm Orange Red 32A, then Yellow Green 148D to lower 6 mm White NN155B); showy 2 to 3 lobed corollas to 15 mm long and 4 mm wide, tubular on the bottom with the lobes spread out like a fan, glabrous on both sides, back side color Red Purple 59B, inside color Red 45A; pistil 9 mm long, ovary 4 mm long, White NN155A, style 4 mm long Red Purple 59C, 2-branched stigma spreading 2 mm wide, Greyed Purple 187A; stamen 5 mm long, anthers 2 mm long and Greyed Purple 187A, filaments 3 mm long, White 155A, pollen none.
*Phyllaries.*—In 4 leafy series, area 2.5 cm wide and 5 mm deep, lobes lanceolate in shape, slightly reflexed, grow to 5 mm long and 3 mm wide, Yellow Green 146B, margins strigose, tip acute, strigose on both sides.
*Receptacle.*—Grows to 10 mm wide and 10 mm deep, White 155A.
*Bloom period.*—July through October in Canby, Oreg.
*Fragrance.*—Floral.
*Lastingness.*—Each inflorescence lasts about two weeks in Canby, Oreg.

Seeds: None seen.
*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

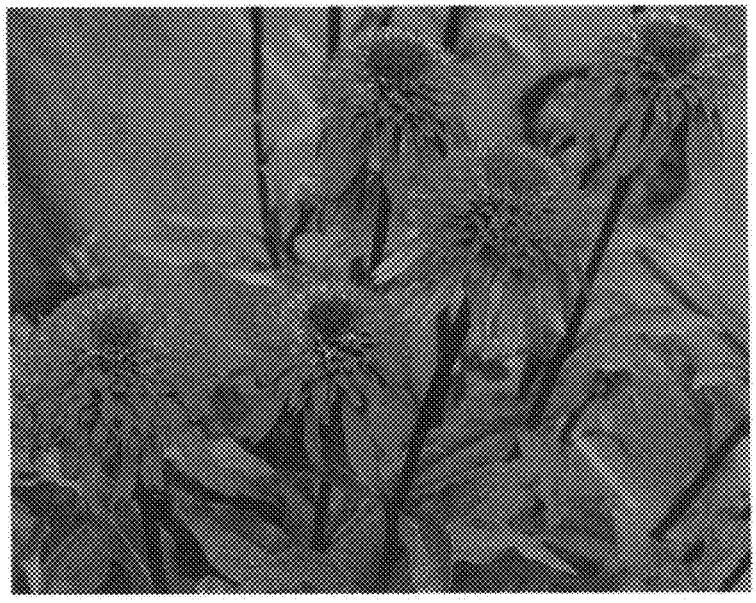

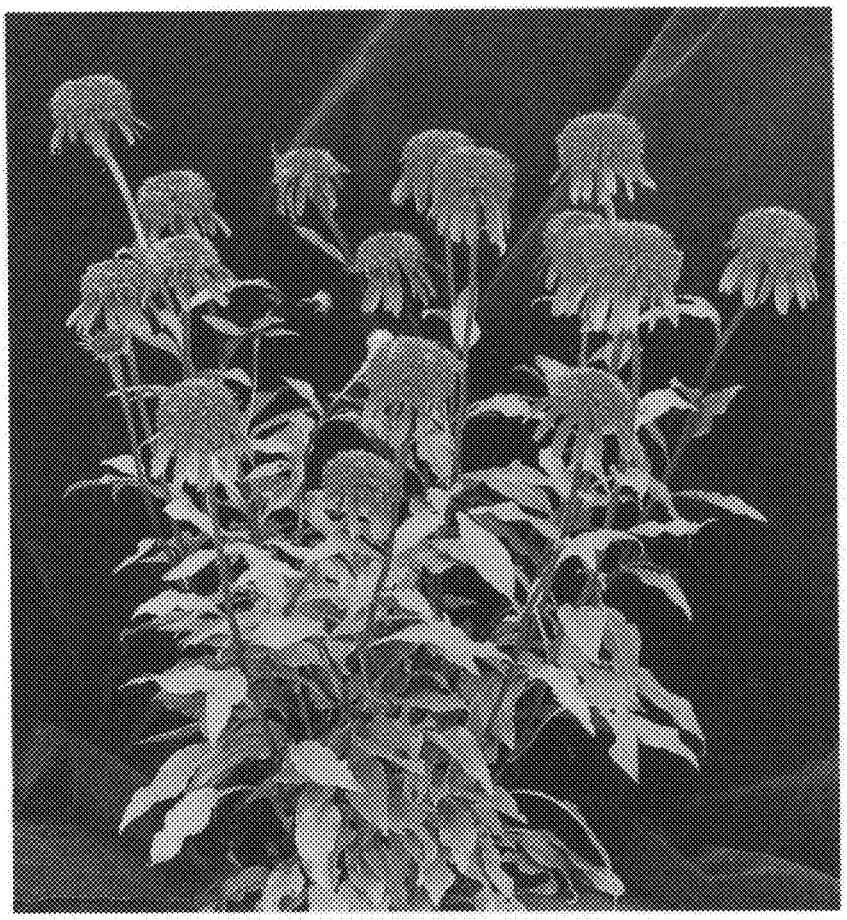
FIG. 1, above, FIG. 2 below